(12) United States Patent
Marble

(10) Patent No.: US 8,562,552 B1
(45) Date of Patent: Oct. 22, 2013

(54) EMERGENCY QUICK SPLINT

(76) Inventor: Alan Forest Marble, Tucson, AZ (US)

( * ) Notice: Subject to any disclaimer, the term of this patent is extended or adjusted under 35 U.S.C. 154(b) by 750 days.

(21) Appl. No.: 12/316,335

(22) Filed: Dec. 10, 2008

(51) Int. Cl.
*A61F 5/00* (2006.01)

(52) U.S. Cl.
USPC .................................. 602/32; 602/5

(58) Field of Classification Search
USPC .......... 602/5, 12, 13, 20, 23, 32–40; 128/869, 128/870, 877, 878, 882
See application file for complete search history.

(56) References Cited

U.S. PATENT DOCUMENTS

| | | |
|---|---|---|
| D235,927 S | 7/1975 | Moore |
| 4,209,011 A | 6/1980 | Peck et al. |
| 4,383,526 A | 5/1983 | Robins |
| 4,520,806 A | 6/1985 | Miller |
| 4,580,555 A | 4/1986 | Coppess |
| 4,708,131 A | 11/1987 | Kendrick |
| 5,074,289 A | 12/1991 | Leibinsohn |
| 5,101,815 A | 4/1992 | Langdon-Orr et al. |
| 5,146,932 A | 9/1992 | McCabe |
| 5,385,534 A | 1/1995 | Cassford |
| 5,456,659 A | 10/1995 | Gildersleeve et al. |
| 5,609,567 A | 3/1997 | Kennedy et al. |
| 5,718,669 A | 2/1998 | Marble |
| 5,891,066 A | 4/1999 | Borschneck et al. |
| 6,109,267 A | 8/2000 | Shaw et al. |
| 6,152,893 A | 11/2000 | Pigg et al. |
| 6,240,923 B1 | 6/2001 | Barrick |
| 6,678,989 B1 | 1/2004 | Lowe |
| 6,991,612 B2 | 1/2006 | Scheinberg et al. |
| 7,037,284 B2 | 5/2006 | Lee |
| 7,131,955 B2 * | 11/2006 | Price et al. ...................... 602/36 |
| 2007/0287946 A1 * | 12/2007 | Kendrick ........................ 602/36 |

FOREIGN PATENT DOCUMENTS

WO WO/2006/002484 12/2006

* cited by examiner

*Primary Examiner* — Patricia Bianco
*Assistant Examiner* — Keri J Nelson
(74) *Attorney, Agent, or Firm* — Hayes Soloway P.C.

(57) ABSTRACT

A splint is provided having a framesheet with a pocket to receive a rigid tube. The framesheet is secured about the injured limb by a plurality of dynamic closure straps. An optional traction bar having a cantilever arm and adjustable link is inserted on the end of the collapsible rigid tube, and connected to a harness that applies traction to the limb. The countertraction force is dissipated throughout the entire framesheet, eliminating externally applied pressure points against contiguous anatomy.

20 Claims, 11 Drawing Sheets

EMERGENCY QUICK SPLINT

CROSS-REFERENCE TO RELATED APPLICATIONS

This application claims priority from U.S. Provisional Application Ser. No. 60/922,941, filed Apr. 11, 2007.

FEDERALLY SPONSORED RESEARCH

None

SEQUENCE LISTING

None

BACKGROUND

1. Field of Invention

This invention relates to long bone splints, specifically to an improved upper and lower extremity long bone splint that provides rigid long-axis immobilization with integrated balanced traction and off-axis stabilization capability.

2. Prior Art

Our military tactical combat care medics are encountering massive bony and soft-tissue injury from explosive IED and high-energy GSW to pelvis and lower extremities from an enemy who has effectively learned to inflict wounds below body armor. This invention is specifically designed to meet the needs of our military tactical combat care medics for a compact, lightweight, rapidly applied multi-purpose, multi-functional emergency quick splint that can effectively deliver rigid immobilization to both upper and lower extremity long bones, integrate dynamic balanced traction and off-axis stabilization when indicated by casualty presentation, and contain bony and associated massive soft-tissue injury from high-energy GSW, explosive IED trauma and low-energy crush injuries with one easy to use splint, that can be used effectively in combat, terrorist and WMD hot zones.

Today's tactical combat care medic typically does not carry commercial rigid long bone splints due to size and bulk. Long bone splints are usually improvised in the field by combining multiple formable splints in an attempt to achieve necessary length, strength and support for effective long bone immobilization. These formable splints were originally developed by Scheinberg, U.S. Pat. No. 6,991,612 for use on hands, wrists, forearms, and ankles. These formable splints have a malleable metal core that is covered by a layer of synthetic foam padding material on each of its opposite sides, and stow flat or rolled. This type of formable splint as a stand alone long bone immobilization device, lacks required long axis rigidity, length and width required to effectively manage massive bony and soft-tissue trauma experienced by today's hot zone casualties, but are excellent splints when used as originally designed to immobilize distal extremity trauma.

Collapsible single pole traction splints carried by tactical combat care medics were originally developed by Kendrick, U.S. Pat. No. 4,708,131. These collapsible single pole traction splints are applied laterally to a lower extremity. This type of traction splint requires a manual in-line distal tractive force be applied to an ankle harness (a pulling force on an ankle harness), with counter-traction force derived from a narrow webbing sling type strap looped around the medial groin soft-tissue to make the splint work. The force of the ankle harness pulling on the looped strap at the groin is contraindicated when associated with pelvic and hip trauma, limiting tactical effectiveness and use when pelvic and/or hip trauma may have occurred. This contraindication also prohibits use on upper extremities, as applied counter-traction force against limb root (about the shoulder and armpit) would occlude major blood vessels and compress the brachial plexus, possibly causing corollary trauma.

One aspect of the invention provides an in-line biomechanical traction force that maintains counter-traction force to the proximal end of the splint itself, not on the injured patient's limb root anatomy. The entire splint surface area in contact with the injured extremity anatomy functions as a counter-traction anchor. Applied biomechanical forces are thus dissipated and balanced throughout the whole splint, eliminating externally applied pressure against the limb root, eliminating possible contraindications.

When traction is applied to the ankle harness of an injured extremity using the collapsible single pole of the prior art, the force from the ankle harness exerts pressure on the web strap near the limb root, pulling the strap down toward the ankle harness. The counter traction force causes the unsupported collapsible single pole to bow laterally away from injured extremity. Mid-pole lateral deviation is significant, comparable to a long bow shaft when a taught string is applied to the extremities. To reduce this deviation, wide elastic bands are applied to hold the collapsible single pole to the injured extremity. The wide elastic bands bowing of the pole at the expense of using the injured leg to hold the pole in place. This known collapsible single pole structural deficiency is thought to be corrected, as documented in application instructions, by simply applying wide elastic band at knee prior to traction application, which is in effect using the injured extremity to splint the splint.

A preferred embodiment of this invention uses integrated dynamic quantified traction only to counter the natural tendency of the muscle to pull the distal bone end toward the injury, not for splint structure or to immobilize injured extremity as a whole. An anatomically shaped framesheet (10) includes a pocket (16) configured to be span the length of the underside of the injured leg and to receive a collapsible rigid tube (104). The tube (104) is used to provide rigidity to the splint and provides a site to attach a traction bar (110). A plurality of orbital dynamic closure straps (106) transforms framesheet (10) into a custom fitting posterior enveloping support platform. The support on the posterior of the injured extremity overcomes gravity effects on the injured extremity and provides an anchor point to which counter-traction forces may be applied. The posterior support wrapped around the injured extremity achieves realignment of soft tissue and bony structures along their original lines, while simultaneously containing massive soft-tissue trauma, tamponade hemorrhage and preventing aggravating movement.

Further, this invention stands in sharp contrast to prior art originally developed by Marble, U.S. Pat. No. 5,718,669 that provides integrated rigid, pneumatic, formable vacuum and traction means of immobilization. The integrated splint of the prior art requires multiple sizes to treat both upper and lower extremities, and is too bulky in cubic storage inches to be carried by military tactical combat care medics in hot zones. Most importantly, in a desert combat theater the polystyrene beads used for off-axis structure in the '669 patent during vacuum application retain environmental ambient heat and are subject to direct sunlight thermal heat retention. The heat retention properties of the polystyrene beads makes application, exposure and storage of the splint a challenge. WMD environments require splint removal, decontamination and reapplication in a warm zone, a process that cannot be performed with the polystyrene bead structure of the '669 patent.

Additionally, any integrated traction in the prior art is not quantifiable lending to improper application in use in the field.

A preferred embodiment of this invention utilizes an integrated traction bar (110) with a dynamic quantifiable cantilever arm (30) to apply and quantify applied traction. Prior art traction splints generally need to apply 10% of the injured person's body weight up to a maximum of 15 pounds in traction just to make the splint work. This invention provides injury immobilization through the custom fitted posterior support wrapped around the leg and only uses integrated dynamic traction to balance contractive muscle pull and stabilize distal bone end retraction, rarely exceeding 5 pounds of applied traction.

SUMMARY

This present invention is specifically designed to meet the needs of our military tactical combat care medics for a compact, lightweight, rapidly applied emergency quick splint that delivers efficacious rigid long bone immobilization, and optionally capable of integrating quantified dynamic balanced traction, or off-axis stabilization when such traction or off-axis stabilization is indicated by casualty presentation. A preferred embodiment provides for effective containment of massive bony and soft-tissue injury from high-energy GSW, explosive IED trauma and low-energy crush injuries from an immobilizing posterior enveloping platform that can remain on the casualty during transport from a remote combat hot zone, through CASEVAC triage and to theater surgeons. The invention provides a framesheet (10) with a generally anatomic shape and a narrow tube pocket (16) on the long axis of the framesheet. The pocket (16) is configured to receive a collapsible rigid tube (104). The framesheet further provides a plurality of adjustable dynamic closure straps (106) to custom fit the framesheet to envelop the injured extremity. The posterior support provided by the rigid tube and the enveloping sheet overcomes gravity effects, achieves realignment of soft tissue and bony structures along their original lines, contains massive soft-tissue trauma and tamponade hemorrhage and prevents aggravating movement.

When distal bony retraction occurs from muscle contraction in the injured extremity, a traction bar (110) is inserted into the collapsible rigid tube (104). The traction bar has a dynamic quantifiable cantilever arm (30) and an adjustable linkage. The traction bar is further connected to a kinetic extremity harness (108) to apply biomechanical traction to counteract distal bone retraction with resulting counter-traction force. The counter-traction force is dissipated throughout said framesheet (10) removing externally applied pressure points against contiguous anatomy. The elimination of the pressure also alleves contraindications for use with associated hip or pelvic trauma, and prevents sciatic nerve compression and neurovascular compromise at the limb root, effectively extending the time that the splint can be applied to the casualty in the field. When injury occurs at the joint of a long bone and immobilization of the injured extremity in the position in which the casualty is found is required, off-axis adaptor (120) is placed in collapsible rigid tube (104) creating an articulating joint that allows the framesheet (10) to be angled and applied in off-axis position. In addition, anatomic stabilizer (128) may secure the injured extremity as a unit against the body of the casualty.

DRAWINGS

Figures

In the drawings, closely related figures have the same number but different alphabetic suffixes.

DRAWINGS - REFERENCE NUMERALS

| 10 | framesheet | 12 | base band |
|---|---|---|---|
| 14 | loop tape | 16 | tube pocket |
| 18 | wear pad | 20 | tube |
| 22 | internal ferrule | 24 | elastic cord |
| 26 | dowel pin hole | 28 | rod |
| 30 | cantilever arm | 32 | calibration mark |
| 34 | compression spring | 36 | dowel pin |
| 38 | traction webbing | 40 | pin indicator slot |
| 42 | threaded bore hole | 44 | webbing slot |
| 46 | peel tip | 48 | male buckle |
| 50 | loop tape back | 52 | indicator spring post |
| 54 | indicator post bore hole | 56 | step hole |
| 58 | hook tape back | 60 | thread |
| 62 | threaded press insert | 64 | twist-lock |
| 66 | elastic belting | 68 | simple loop |
| 70 | hook tape | 72 | extruded hook tape |
| 74 | machine screw | 76 | expansion slot |
| 78 | hydrophobic fabric | 80 | external ferrule |
| 82 | closed-cell foam | 84 | extension tube |
| 86 | ladder lock | 88 | web stop pin |
| 90 | female buckle | 92 | binding tape |
| 94 | back-to-back | 96 | twist-lock assembly |
| 98 | orbital band | 100 | internal ferrule assembly |
| 102 | anatomic pad | 104 | collapsible rigid tube |
| 106 | dynamic closure strap | 108 | extremity harness |
| 110 | traction bar | 112 | harness webbing |
| 114 | ring indicator | 116 | double ring indicator |
| 118 | spring stop | 120 | off-axis adaptor |
| 122 | elastic cord slot | 124 | ferrule receiver |
| 126 | rounded articulating tip | 128 | anatomic stabilizer |
| 130 | belt retainer | 132 | application handle |
| 134 | Limb | | |

DETAILED DESCRIPTION

Figure 1A:
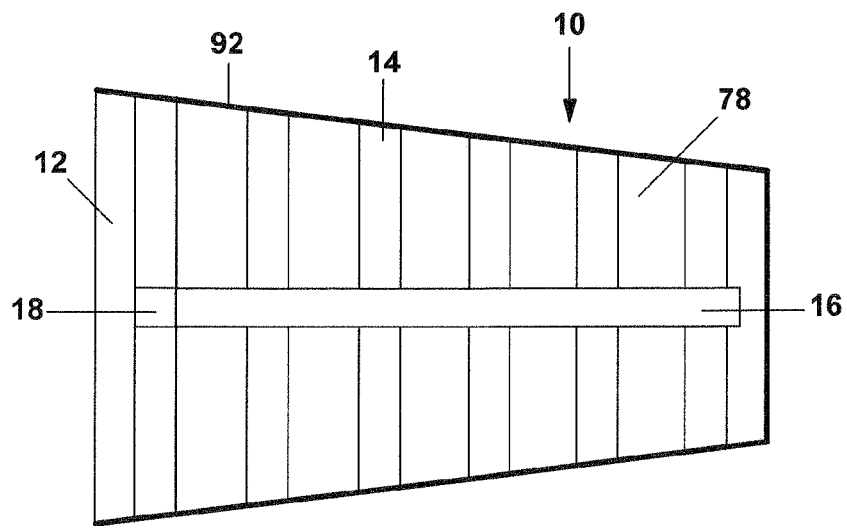
FIG. 1A shows a top plan view of the framesheet (10) in accordance with one embodiment.

FIG. 1A is a plan view of the emergency quick splint framesheet (10) constructed in accordance with one embodiment. Framesheet (10) is shaped to match the anatomy of an injured extremity. In one embodiment, the framesheet (10) is a lightweight sheet of buff textured hypalon coated nylon hydrophobic fabric (78). Sewing thread (60) is a polyester 69-E that has superior strength and excellent resistance to water, chemicals, mildew, abrasion and built in UV inhibitors. The proximal end of the framesheet (10) is constructed by folding framesheet (10) hydrophobic fabric (78) over around a narrow strip of EVA closed-cell foam (82) and sewing the strip in place to form a padded base band (12). The raw horizontal edge created by folding hydrophobic fabric (78) over closed-cell foam (82) is then covered with loop tape (14) facing and sewn in place. Loop tape (14) facing continues in evenly spaced increments down the length of the framesheet (10), to be sewn onto framesheet (10). Long-axis tube pocket (16) is buff textured hypalon coated nylon hydrophobic fabric (78) cut to the same width as the loop tape (14). The proximal base of the pocket (16) is folded back on itself a distance equal to the width of the loop tape (14) and sewn down to form square wear pad (18). Tube pocket (16) with wear pad (18) is then centered on the length of the framesheet (10) over top of loop tape (14) facing and sewn in place leaving distal end open to form tube pocket (16). Framesheet (10) sides and distal end raw edges are bound with stiff polyurethane coated binding tape (92) to finish hydrophobic fabric (78) edges.

Figure 1B:
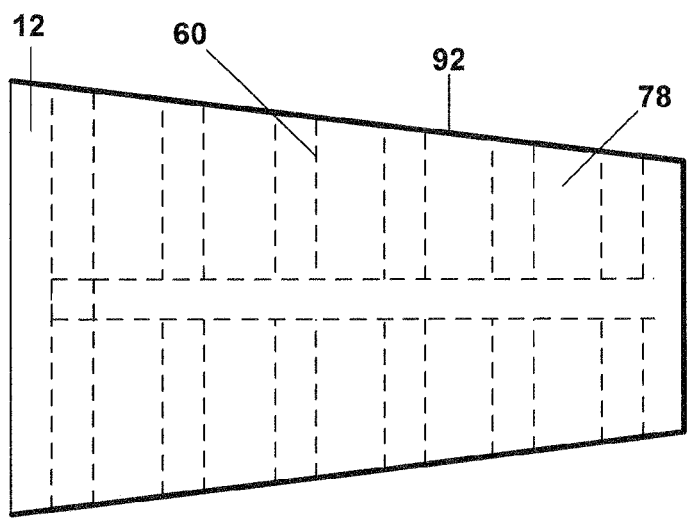
FIG. 1B shows a bottom plan view of the framesheet (10) of FIG. 1A, illustrating the surface that makes contact with the anatomy of a casualty in use.

FIG. 1B is bottom plan view of emergency quick splint framesheet (10) hydrophobic fabric (78) showing thread (60) construction lines from base band (12), loop tape (14) facing and tube pocket (16) top attachment.

Figure 1C:
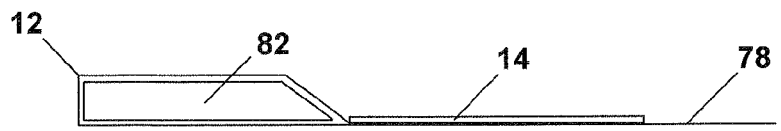
FIG. 1C shows cross-sectional exploded side view of emergency the base band (12) of the framesheet (10).

FIG. 1C is cross-sectional side view of emergency quick splint framesheet (10) proximal base band (12) showing encapsulated EVA closed-cell foam (82) and loop tape (14) placement over hydrophobic fabric (78) fold over edge.

Figure 2A:
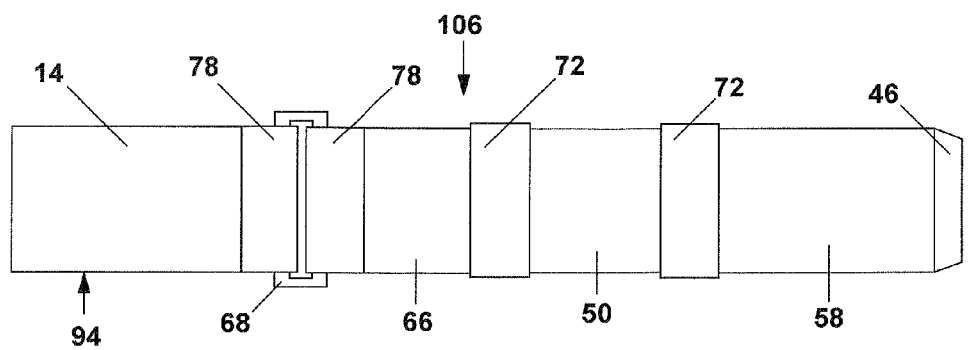
FIG. 2A shows top view of dynamic closure strap (106) in accordance with one embodiment.

FIG. 2A is top view of dynamic closure strap (106) in accordance with one embodiment. Dynamic closure strap (106) is constructed from hot cut back-to-back (94) hook and loop tape attached loop face up to one side of acetal simple loop (68) with hydrophobic fabric (78) hinge. Elastic belting (66) is attached to other side of simple loop (68) with hydrophobic fabric (78) hinge. Elastic belting (66) free end is then sewn to loop tape back (50) and banded with narrow extruded hook tape (72) to cover joint. Loop tape back (50) free end is then sewn to hook tape back (58) and banded with narrow extruded hook tape (72) to cover joint. Hook tape back (58) free end is then ultrasonically welded to form peel tip (46) completing dynamic closure strap (106).

Figure 2B:
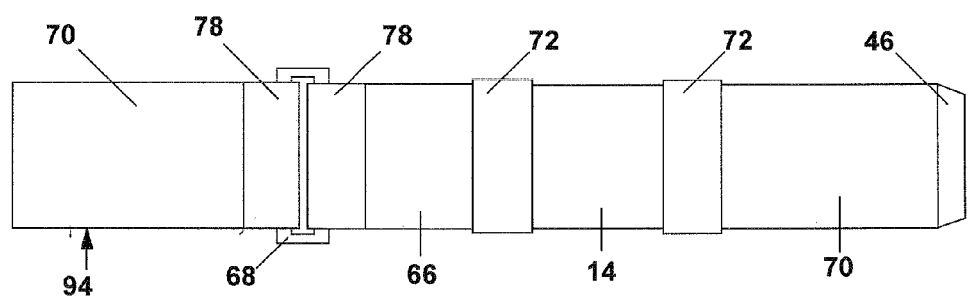
FIG. 2B shows bottom view of dynamic closure strap (106).

FIG. 2B is bottom view of dynamic closure strap (106) that engages framesheet (10) loop tape (14) during closure. Dynamic closure strap (106) engagement side has back-to-back (94) hook face up, attached to simple loop (68) with hydrophobic fabric (78) hinge. Elastic belting (66) is attached to other side of simple loop (68) with hydrophobic fabric (78) hinge with free end sewn to loop tape (14) and joint banded with narrow extruded hook tape (72). Loop tape (14) free end is sewn to hook tape (70) with peel tip (46) and banded with narrow extruded hook tape (72) to cover joint.

Figure 2C:
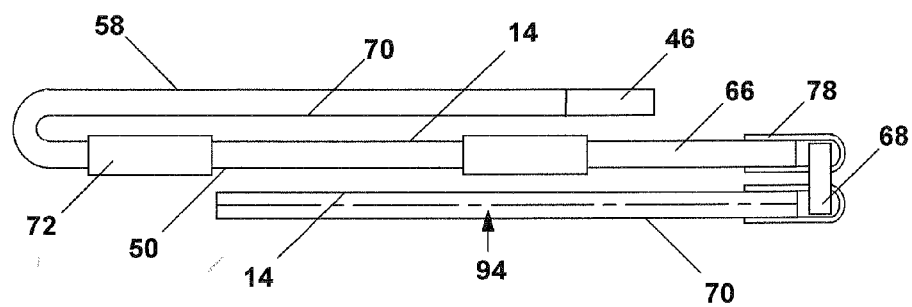
FIG. 2C shows side view of dynamic closure strap (106) in stow ready position.

FIG. 2C shows side view dynamic closure strap (106) in stow ready position when attached to framesheet (10) loop tape (14) bands. Dynamic closure strap (106) back-to-back (94) hook engages framesheet (10) loop tape (14) is folded back on itself at simple loop (68) with narrow extruded hook tape (72) bands engaging back-to-back (94) loop side and framesheet (10) loop tape (14) bands and then hook tape (70) with peel tip (46) is folded down engaging dynamic closure strap (106) loop tape (14) completing stow ready position.

Figure 3A:
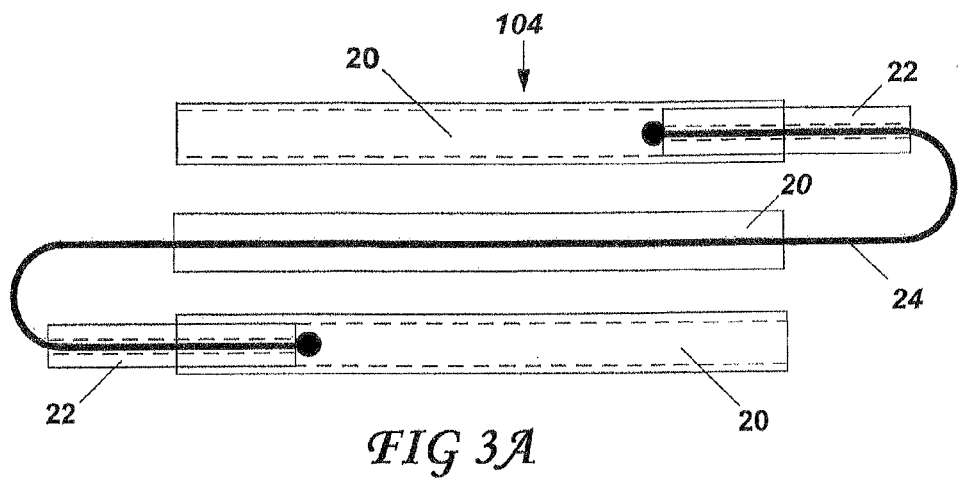
FIG. 3A shows cross-sectional side view of collapsible rigid tube (104) in accordance with one embodiment.

FIG. 3A is cross-sectional side view of collapsible rigid tube (104) tri-folded in accordance with one embodiment to keep emergency quick splint compact. Tube (20) is a fiberglass filament wound epoxy resin matrix with axial and biaxial fiber orientation for maximum deflection strength. Tube (20) is flame resistant, strong, durable, and exhibits uncommon dimensional stability impervious to high humidity or immersion. Tube (20) is center less ground to within dimensional tolerance, then cut with carbide or diamond saw into three equal sections, and ends chamfered on lathe. Internal ferrule (22) is inserted into two of the three tube (20) sections making internal ferrule assembly (100). Nylon sheathed elastic cord (24) is knotted and threaded through first internal ferrule assembly (100) with knot seating against internal ferrule (22), then threaded through tube (20), then threaded into second internal ferrule assembly (100) starting from internal ferrule (22) end and threading through until protruding from end of tube (20). Elastic cord (24) is then tensioned and knotted under tension at end of tube (20) with excess elastic cord (24) trimmed off and allowed to retract into internal ferrule assembly (100) with knot seating under tension against internal ferrule (22). This method of construction assures elastic cord (24) remains under tension when collapsible rigid tube (104) is assembled for use.

Figure 3B:
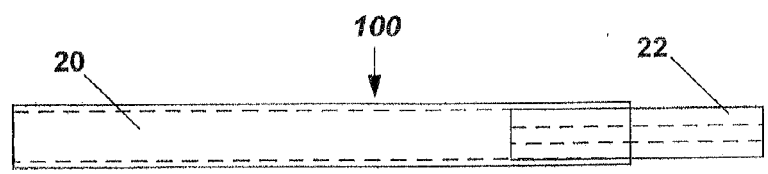
FIG. 3B shows cross-sectional side view of internal ferrule assembly (100) of the collapsible rigid tube (104).

FIG. 3B shows cross-sectional side view of collapsible rigid tube (104) internal ferrule assembly (100) which is constructed using internal ferrule (22) and tube (20). Internal ferrule (22) is a fiberglass filament wound epoxy resin matrix rod that is center-less ground to tube (20) inside diameter, then cut to length and center hole bored for nylon covered elastic cord (24) insertion. Internal ferrule (22) ends are chamfered, inserted halfway into tube (20) and secured in place with cynoacrelate medium viscosity adhesive.

Figure 3C:
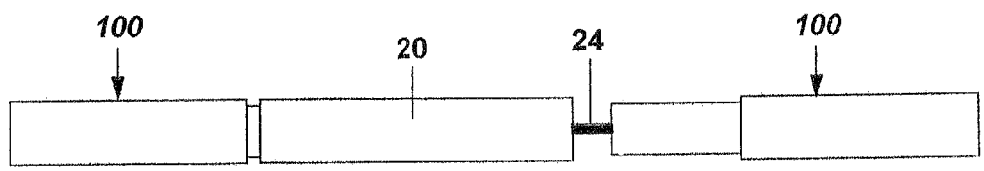
FIG. 3C shows side view of internal ferrule assembly (100) with partial in-line assembly to tube (20) and opposing end internal ferrule assembly (100) extended from tube (20).

FIG. 3C shows side view of collapsible rigid tube (104) partial in-line assembly with internal ferrule assembly (100) connecting into tube (20) and opposing internal ferrule assembly (100) disconnected from tube (20) with elongation of elastic cord (24).

Figure 3D:
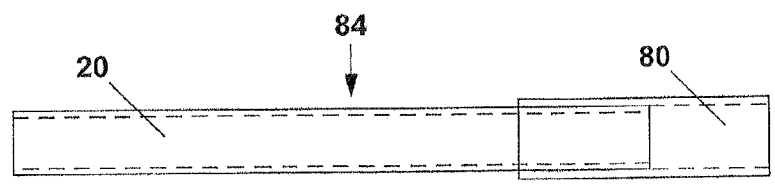
FIG. 3D shows cross-sectional side view of extension tube (84) assembly.

FIG. 3D shows cross-sectional side view of collapsible rigid tube (104) extension tube (84) which are constructed using an external ferrule (80) and tube (20). External ferrule (80) is constructed from high density polyethylene HDPE rod cut and surfaced, and then a center hole is bored to outside diameter of tube (20) for insertion. External ferrule (80) ends are chamfered, then inserted halfway onto tube (20) and secured in place with conduit adhesive that bonds fiberglass to HDPE.

Figure 4A:
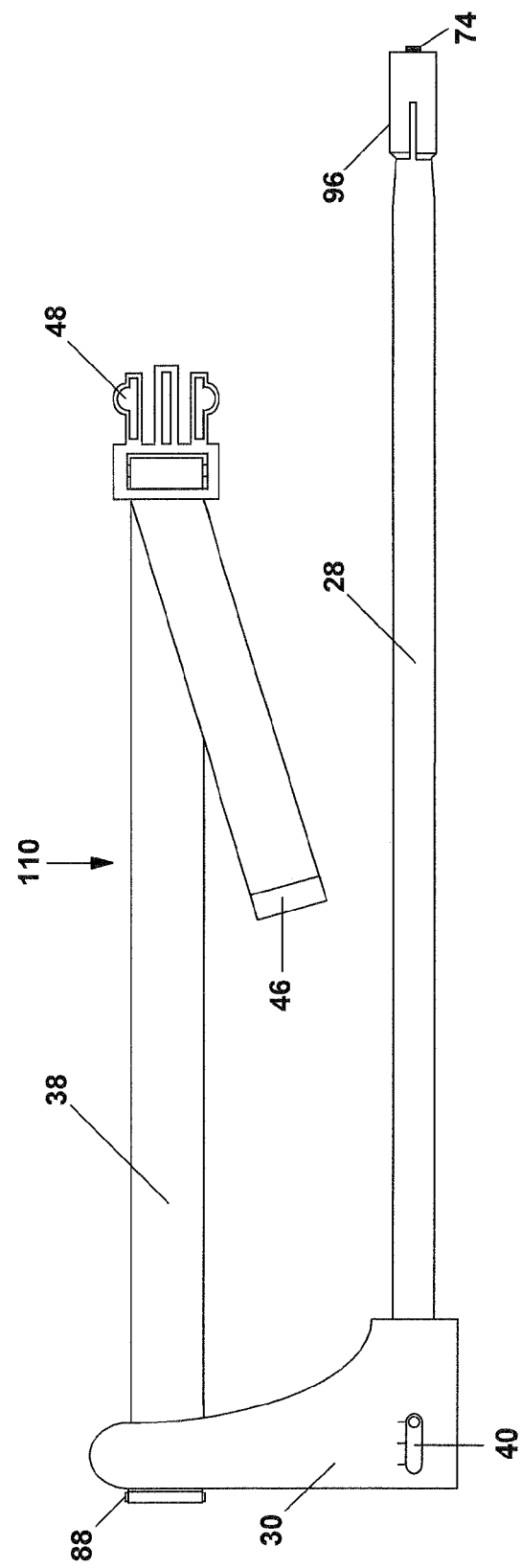
FIG. 4A shows side view of quantifiable dynamic traction bar (110) in accordance with one embodiment.

FIG. 4A shows side view of quantifiable dynamic traction bar (110) in accordance with one embodiment. Rod (28) is constructed from 7075 T-6 aircraft aluminum cut to length with both ends machine finished. One end receives twist-lock assembly (96) that moves up and down on rod (28) tapered end, varying the length of the traction bar assembly and causing expansion or contraction in twist-lock (64). Opposing end of rod (28) receives cantilever arm (30) that is machined from HDPE. Cantilever arm (30) is slotted to receive traction webbing (38) with male buckle (48) for traction application. Traction webbing (38) is prevented from slipping through cantilever arm (30) slot by web stop pin (88) and opposite end prevents male buckle (48) from sliding off traction webbing (38) with peel tip (46). Cantilever arm (30) compresses on rod (28) under applied traction forces which are quantified at pin indicator slot (40).

Figure 4B:
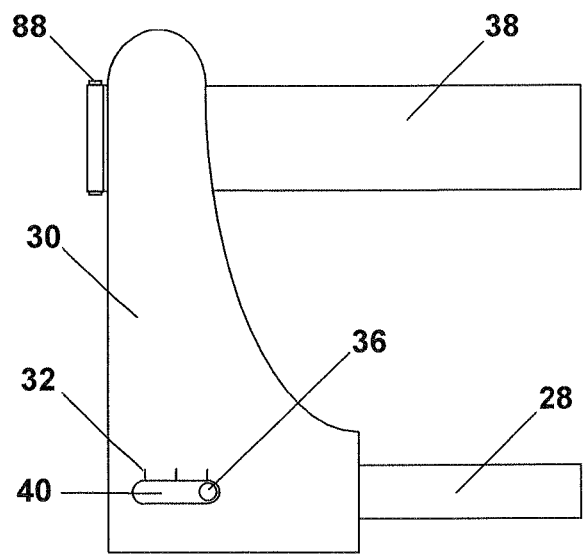
FIG. 4B shows exploded side view of quantifiable dynamic traction bar (110) cantilever arm (30).

FIG. 4B shows partial side view quantifiable dynamic traction bar (110) with cantilever arm (30) having traction webbing (38) threaded through webbing slot (44) and seated in position function by web stop pin (88) that prevents pass through. Traction webbing (38) is cut to length with one end folded over and ultrasonically welded forming peel tip (46) and opposing end folded over nylon line thicker than webbing slot (44) and ultrasonically welded in place with ends trimmed and sealed by hot knife forming web stop pin (88). Traction bar (110) cantilever arm (30) pin indicator slot (40) calibration mark (32) are used to quantify amount of mechanical traction applied. Dowel pin (36) connects cantilever arm (30) to rod (28) in addition to functioning as traction pin indicator in quantifiable pin indicator slot (40) when forces are applied.

Figure 4C:
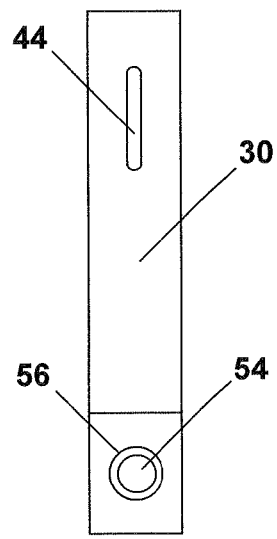
FIG. 4C shows back view of cantilever arm (30).

FIG. 4C shows back view of cantilever arm (30) with milled webbing slot (44) and rod (28) receiving step hole (56) with smaller continuing indicator post bore hole (54).

Figure 4D:
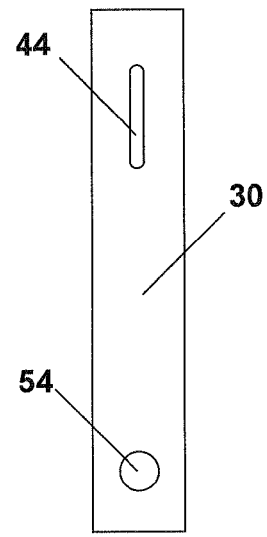
FIG. 4D shows front view of cantilever arm (30).

FIG. 4D shows front view of cantilever arm (30) with milled webbing slot (44) and indicator post bore hole (54).

Figure 4E:
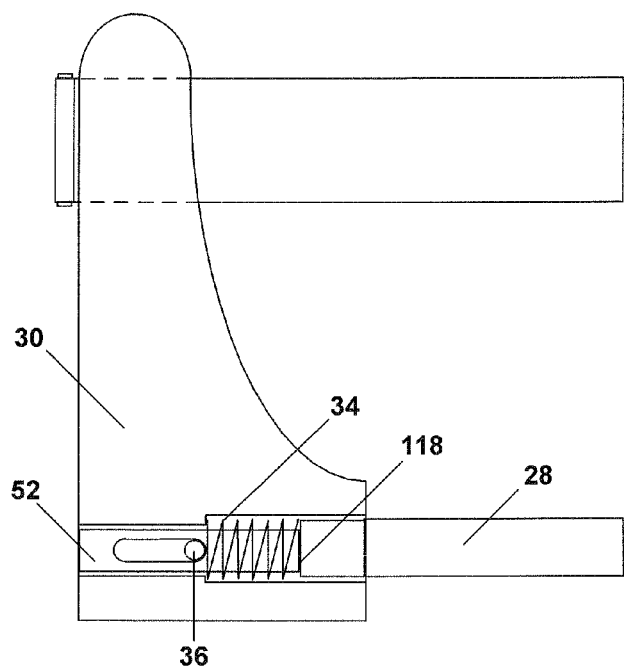
FIG. 4E shows cross-sectional side view of quantifiable dynamic traction bar (110) with cantilever arm (30) in neutral compression position.

FIG. 4E shows cross-sectional side view of cantilever arm (30) in a neutral position. Dowel pin (36) and compression spring (34) are in neutral position with no compression applied. Rod (28) indicator spring post (52) is flush with cantilever arm (30) front indicating no traction is being applied.

Figure 4F:
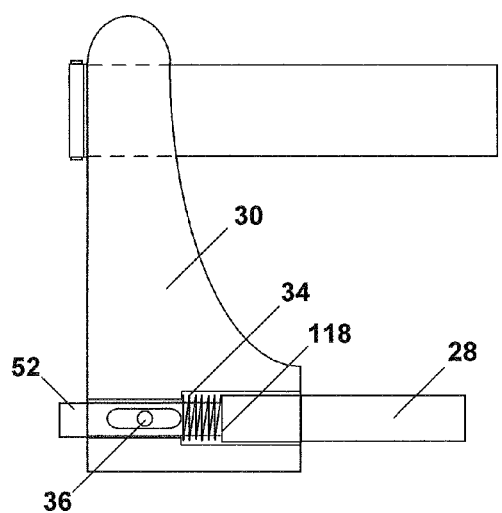
FIG. 4F shows cross-sectional side view of quantifiable dynamic traction bar (110) with cantilever arm (30) in 50% compression position.

FIG. 4F shows cross-sectional side view of cantilever arm (30) in 50% compression position. Dowel pin (36) positioned midway in pin indicator slot (40) and compression spring (34) is 50% compressed, indicating that approximately seven pounds of traction has been applied. Rod (28) indicator spring post (52) is now protruding from cantilever arm (30) front with ring indicator (114) visible indicating seven pounds of traction has been applied to injured extremity.

Figure 4G:
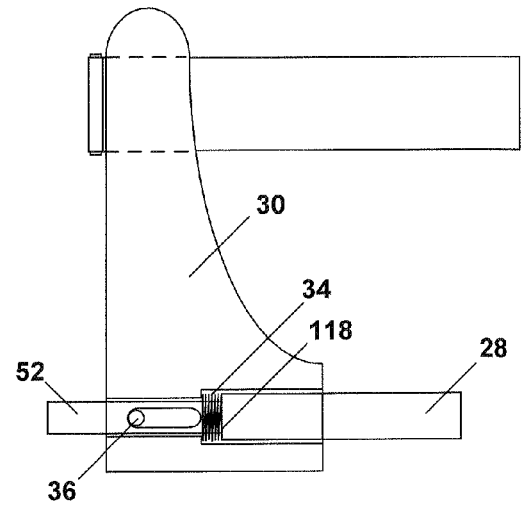
FIG. 4G shows cross-sectional side view of quantifiable dynamic traction bar (110) with cantilever arm (30) in 100% compression position.

FIG. 4G shows cross-sectional side view of cantilever arm (30) in 100% compression position. Dowel pin (36) positioned at front end of pin indicator slot (40) and compression spring (34) is 100% compressed. Rod (28) indicator spring post (52) is now protruding from cantilever arm (30) front with double ring indicator (116) visible indicating fifteen pounds of traction has been applied to injured extremity.

Figure 4H:
FIG. 4H shows cross-sectional side view of rod (28).

FIG. 4H shows cross-sectional side view of traction bar (110) rod (28) that is 7075 T-6 aircraft aluminum with cantilever arm (30) end is turned to smaller diameter forming indicator spring post (52) that receives quantified compression spring (34) and forms internal spring stop (118). Traction ring indicator (114) and double ring indicator (116) are formed by turning small grooves in indicator spring post (52) to mark 50% protrusion and 100% protrusion. Dowel pin hole (26) receives dowel pin (36) that holds compression spring (34) in position against spring stop (118). Rod (28) tapered end is to expand twist-lock assembly (96) as it moves up taper tightening against tube (20) sidewall. Tapered end is drilled and taped to form threaded bore hole (42) to receive machine screw (74) that moves twist-lock (64) on rod (28) taper friction locking and unlocking twist-lock (64) from tube (20) sidewall.

Figure 4I:
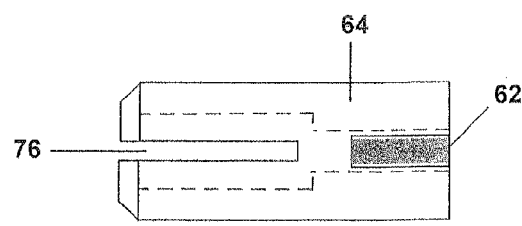
FIG. 4I shows cross-sectional side view of twist-lock (64) with threaded press insert (62).

FIG. 4I shows cross-sectional side view of twist-lock (64) that is machined from HDPE rod to diameter of rod (28) and chamfered on one end. Chamfer end is bored out halfway through twist-lock (64) to receive rod (28) tapered end, with smaller diameter bore hole continuing through for threaded press insert (62). Chamfer end then has two equally spaced expansion slot (76) milled through twist-lock (64) sidewall into bore hole to allow part expansion.

Figure 4J:
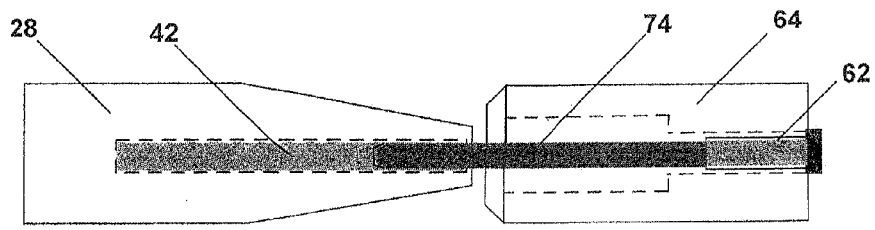
FIG. 4J shows cross-sectional side view of rod (28) tapered end threaded bore hole (42) with twist-lock (64) machine screw (74) partially engaged.

FIG. 4J shows cross-sectional side view of rod (28) tapered end with threaded bore hole (42) receiving machine screw (74) that has been completely threaded into twist-lock (64) threaded press insert (62) filled with thread locking adhesive forming twist-lock assembly (96).

Figure 4K:
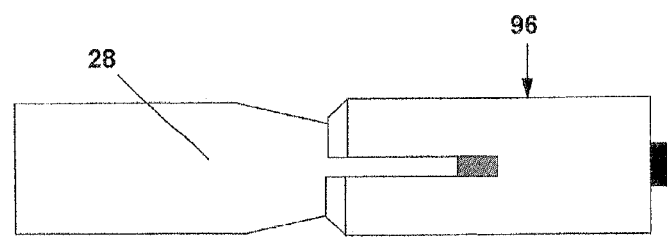
FIG. 4K shows detailed side view of rod (28) tapered end with twist-lock assembly (96) in engagement ready position.

FIG. 4K shows side view of twist-lock assembly (96) turned onto rod (28) in an application ready position which can now be inserted into tube (20) to desired length and tightened in place.

Figure 5A:
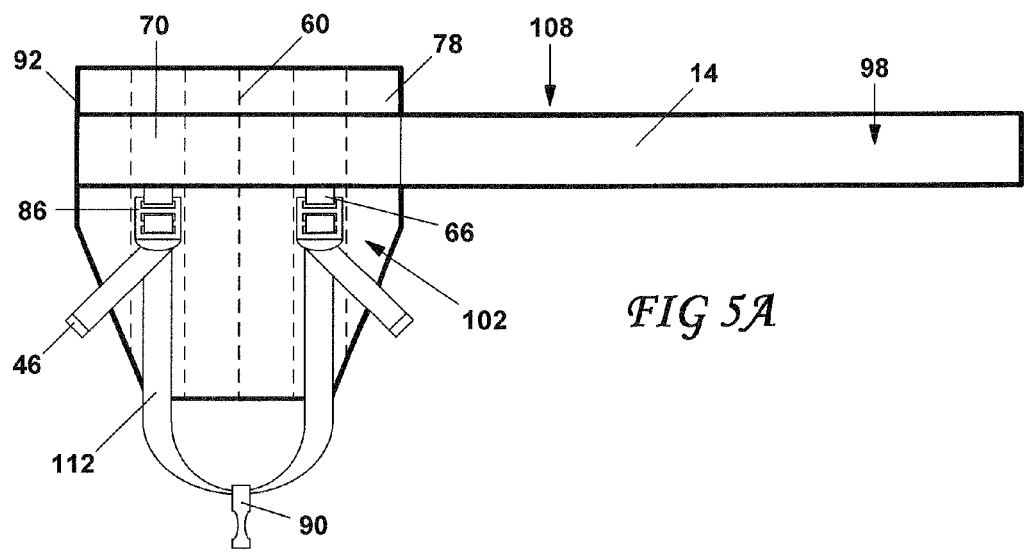
FIG. 5A shows front view of extremity harness (108) with orbital band (98) and dynamic harness webbing (112) in accordance with one embodiment.

FIG. 5A shows front view extremity harness (108) in accordance with one embodiment. Extremity harness (108) wraps around the distal extremity with orbital band (98). Anatomic pad (102) assembly is constructed from front and back polygon like shaped sheets lightweight buff textured hypalon coated nylon hydrophobic fabric (78), and one polygon like shaped sheet of EVA closed-cell foam (82). Front hydrophobic fabric (78) sheet has two elastic belting (66) straps formed into loops with attached acetal ladder lock (86) and sewn on where ends will be covered by orbital band (98) hook tape (70) attachment. Orbital band (98) is constructed by cutting hook tape (70) same width as hydrophobic fabric (78) front, and two pieces of loop tape (14) twice as long, then ultrasonically welding hook tape (70) edge to edges of both loop tape (14) pieces placed back to back. An extruded hook tape (72) end tip is sewn to orbital band (98) back loop tape (14) at tip, and then all raw edges are bound with stiff polyurethane coated binding tape (92) forming orbital band (98) with finished look. Orbital band (98) hook tape (70) section is positioned on hydrophobic fabric (78) front covering elastic belting (66) attachment and sewn in place, with remaining orbital band (98) extending off right side of hydrophobic fabric (78) front. Hydrophobic fabric (78) front outside edges are now sewn to polygon like shaped sheet of EVA closed-cell foam (82). Then starting from top center a thread (60) vertical line break is sewn through hydrophobic fabric (78) and closed-cell foam (82), over top of orbital band (98) hook tape (70) section, repeated evenly on each side of center thread (60) vertical line break entire width of hydrophobic fabric (78) front for anatomic conformity. Bottom hydrophobic fabric (78) is now sewn to outside edges of closed-cell foam (82) creating solid back without vertical line breaks. Then outside raw edges are bound with stiff polyurethane coated binding tape (92) for smooth extremity contact surfaces and finished look. Harness webbing (112) is of functional length and with ultrasonically welded peel tip (46) on each end to prevent inadvertent dislodgement from ladder lock (86) tensioning bars and remain in position of use. Side release female buckle (90) is threaded onto harness webbing (112) to as a means to connect to traction bar (110) male buckle (48).

Figure 5B:
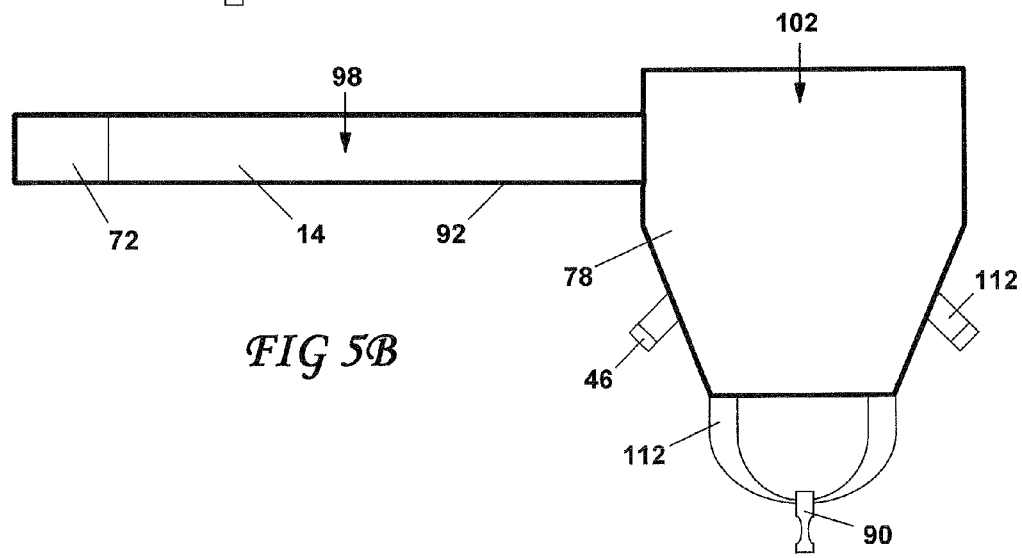
FIG. 5B shows back view of extremity harness (108) orbital band (98) and anatomic pad (102) that provides injured extremity posterior support.

FIG. 5B is back view of extremity harness (108) that makes contact with anatomy. Anatomic pad (102) back is constructed without thread (60) vertical line breaks sewn through buff textured hypalon coated nylon hydrophobic fabric (78) covering to eliminate sewing needle perforation holes. Orbital band (98) has finished look with custom extremity fitting circumferential wrap with extruded hook tape (72) engagement tip.

Figure 5C:
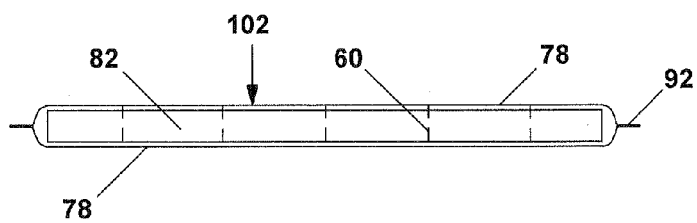
FIG. 5C shows cross-sectional side view of extremity harness (108) anatomic pad (102) encapsulating closed-cell foam (82).

FIG. 5C shows cross-sectional side view anatomic pad (102). Closed-cell foam (82) is covered with buff textured hypalon coated nylon hydrophobic fabric (78) with outside raw edges bound with stiff polyurethane coated binding tape (92) to finish raw edge.

Figure 6A:
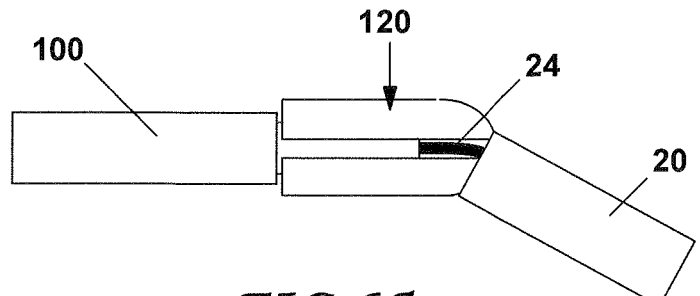
FIG. 6A shows side view of off-axis adaptor (120) installed on collapsible rigid tube (104) in off-axis position in accordance with one embodiment.

FIG. 6A shows side view of off-axis adaptor (120) installed between collapsible rigid tube (104) internal ferrule assembly (100) and tube (20) joint tensioned in an angled position of function by elastic cord (24) in accordance with one embodiment.

Figure 6B:
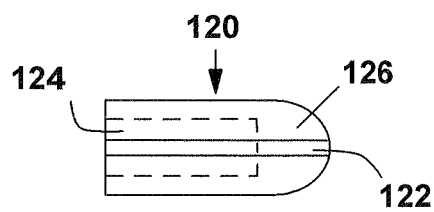
FIG. 6B shows cross-sectional side view of off-axis adaptor (120).

FIG. 6B shows cross-sectional side view of off-axis adaptor (120) machined from high density polyethylene rod with rounded articulating tip (126) on one end and ferrule receiver (124) on opposing end with elastic cord slot (122) is milled into entire length of off-axis adaptor (120) radius depth.

Figure 6C:
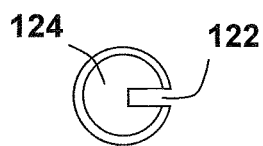
FIG. 6C shows end view of off-axis adaptor (120) that receives internal ferrule assembly (100).

FIG. 6C shows end view of off-axis adaptor (120) that receives internal ferrule assembly (100). Ferrule receiver (124) is milled to outside diameter of internal ferrule (22) and depth of protruding from internal ferrule assembly (100). Elastic cord slot (122) is milled into entire length of off-axis adaptor (120) at radius depth.

Figure 6D:
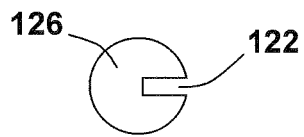
FIG. 6D shows end view of off-axis adaptor (120) rounded articulating tip (126) that receives tube (20).

FIG. 6D shows opposing end view of off-axis adaptor (120) rounded articulating tip (126) that receives tube (20). Rounded articulating tip (126) is milled at an arc that permits uniform movement without interfering with elastic cord slot (122) when tensioned to tube (20).

Figure 7A:
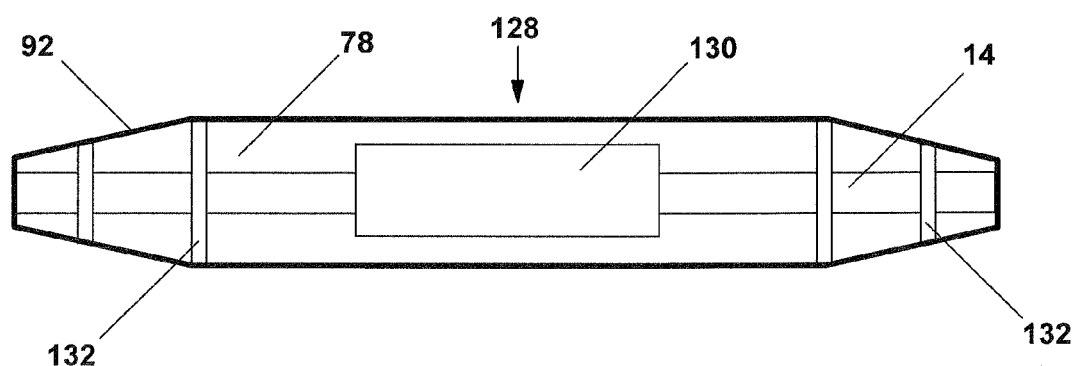
FIG. 7A shows back view of anatomic stabilizer (128) in accordance with one embodiment.

FIG. 7A shows front view of anatomic stabilizer (128) in accordance with one embodiment. Anatomic stabilizer (128) attaches around the hip and pelvic areas superior to FIG. 1A emergency quick splint framesheet (10) to stabilize the hip and pelvic areas. Anatomic stabilizer (128) is rectangular shaped sheet with tapered ends, constructed from buff textured hypalon coated nylon hydrophobic fabric (78). Loop tape (14) belt is sewn entire length on center. Static belt retainer (130) is buff textured hypalon coated nylon hydrophobic fabric (78) that is cut rectangle shaped and centered on anatomic stabilizer (128) sheet and sewn down on horizontal edges to form sleeve with open ends. Four application handle (132) are cut from buff textured hypalon coated nylon hydrophobic fabric (78) and two are sewn on near each end of anatomic stabilizer (128) sheet, and two between belt retainer (130) and each end application handle (132). Anatomic stabilizer (128) sheet outside raw edges are bound with stiff polyurethane coated binding tape (92) to give edge body stiffness, speed application and finish raw edge. A static compression belt constructed from seat belt type nylon webbing with hooded side release buckle. Static compression belt is threaded through belt retainer (130) and under application handle (132) for use or in place storage. FIG. 2A dynamic closure strap (106) is attached to loop tape (14) belt where needed to provide dynamic closure.

Figure 7B:
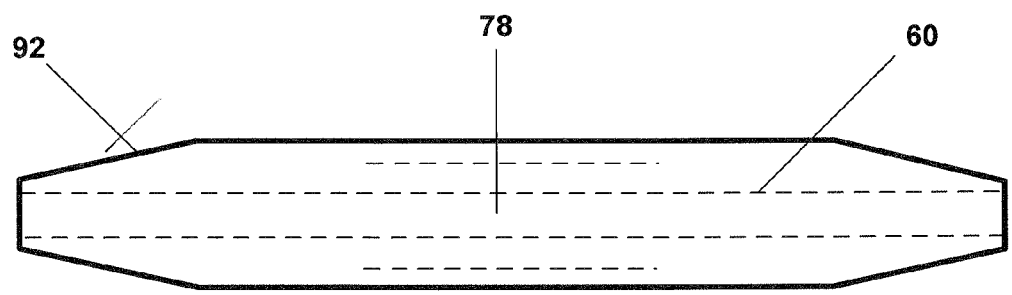
FIG. 7B shows front view of anatomic stabilizer (128).

FIG. 7B is back view of anatomic stabilizer (128) sheet showing binding tape (92) on edge of hydrophobic fabric (78), and thread (60) construction lines from loop tape (14) and belt retainer (130) attachment.

Operation

The preferred embodiment of this invention is specifically designed to meet the needs of our military tactical combat care medics for a compact, lightweight, rapidly applied, multipurpose, multifunctional, emergency quick splint that can effectively provide rigid immobilization of both upper and lower extremity long bones, deliver integrated dynamic quantifiable balanced traction and off-axis stabilization when indicated by casualty presentation, and contain bony and associated massive soft-tissue injury from high-energy GSW, explosive IED trauma and low-energy crush injuries from within one easy to use splint that can remain on the injured limb (134) of the casualty for extended periods of time.

Emergency quick splint framesheet (10) provides a posterior enveloping immobilization platform for lower extremity injuries when collapsible rigid tube (104) is inserted into posterior long-axis tube pocket (16) and at least one dynamic closure strap (106) is applied beginning at the proximal end of the framesheet (10) and moving to the distal end of the framesheet. The straps are secured with enough force to actuate the elastic belting (66) of the closure strap (106). The tension from the elastic belting wraps the framesheet around the injured extremity with a custom fit, enveloping the limb (134) with support to overcome gravity effects, achieve realignment of soft tissue and bony structures along their original lines, contain massive soft-tissue trauma, tamponade hemorrhaging and prevent aggravating movement.

For upper extremity injuries, framesheet (10) proximal base is folded back to back, onto itself at trailing edge of third proximal loop tape (14) facing with resulting hydrophobic fabric (78) protruding edges tucked underneath. Long-axis collapsible rigid tube (104) with one internal ferrule assembly (100) section folded over is inserted into posterior long-axis tube pocket (16). Dynamic closure strap (106) is applied as above, with enough force to actuate the elastic belting (66). The upper extremity is now under rigid external immobilization with the same results and advantages as described above with regard to a lower extremity.

When rigid long-axis immobilization with traction integration is required to keep the bone from being retracted by muscle contraction, framesheet (10) becomes a posterior enveloping immobilization platform when long-axis collapsible rigid tube (104) is inserted into posterior long-axis tube pocket (16) as described above. The extremity harness (108) is applied to the injured lower extremity with the heel resting on the anatomic pad (102). The orbital band (98) is wrapped about the leg just proximal to the ankle, and the harness webbing (112) is tightened onto the plantar aspect of foot removing excess slack. The framesheet (10) is then placed under injured lower extremity as proximal to the limb root (hip) as possible. A closure strap is then applied in position closest to the patient's hip. Traction bar (110) is attached to collapsible rigid tube (104) approximately four to six inches from plantar aspect of foot, and turned clockwise until twist-lock assembly (96) engages tube (20) sidewall locking into position. Harness webbing (112) with female buckle (90) is connected to male buckle (48) on traction webbing (38) and excess slack is removed by tightening on traction webbing. To assure a smooth traction application with optimal placement of the band (12) of the framesheet (10), one hand is placed on traction bar (110) cantilever arm (30) to hold in place or slightly push in proximal direction, as other hand pulls traction on traction webbing (38) tail in distal direction until dowel pin (36) in pin indicator slot (40) reaches desired calibration mark (32) or position. Indicator spring post (52) will be protruding from cantilever arm (30) front indicating lower extremity injury is under traction. The framesheet (10) is then fully closed by fastening the remaining dynamic closure straps (106) beginning at the position closest to the hip of the patient and proceeding toward the foot.

Anatomic stabilizer (128) may be wrapped around the pelvis, positioned over the trochanters, and closed with a dynamic closure strap (106) to stabilize the hip joint of the injured leg. When rigid long-axis immobilization with traction integration is required to stabilize an upper extremity, framesheet (10) proximal base is folded back to back, onto itself at the trailing edge of third proximal loop tape (14) facing with resulting hydrophobic fabric (78) protruding edges tucked underneath. Long-axis collapsible rigid tube (104) with one internal ferrule assembly (100) section folded over is inserted into posterior long-axis tube pocket (16). Extremity harness (108) is then applied to the injured upper extremity with the orbital band (98) positioned just proximal to the wrist, with the pinky side of the hand resting on the anatomic pad (102) with the thumb up. Orbital band (98) is then wrapped about the forearm, with the harness webbing (112) slack removed.

Prepared framesheet (10) is then placed under the injured extremity as close to the shoulder as possible. A dynamic closure strap (106) is then applied in the position closest to the shoulder. Traction bar (110) is then inserted into the collapsible rigid tube (104) approximately four inches from the hand of the patient and turned clockwise until twist-lock assembly (96) engages the tube (20) sidewall and locks into position. The female buckle of the harness webbing is then connected to the male buckle (48) on the traction webbing (38) and the excess slack removed.

To assure smooth traction application with proximal framesheet (10) placement, one hand may be placed on the cantilever arm (30) of the traction bar (110) to hold in place or slightly push toward the root limb as the other hand tightens the traction webbing (38). Sufficient traction is applied when the dowel pin (36) in the pin indicator slot (40) reaches a desired calibration mark (32) or position. Indicator spring post (52) will also be protruding from cantilever arm (30) front indicating lower extremity injury is under traction.

The framesheet (10) may then be fully secured with the remaining plurality of dynamic closure straps (106), applying from proximal to distal on the arm with enough force to actuate the elastic belting (66) of the strap (106). The Immobilized extremity may then be bound to the torso using the anatomic stabilizer (128) with dynamic closure strap (106) to stabilize the shoulder joint of the injured arm.

When muscle contraction of the injured limb (134) increases the pressure on the traction bar (110), resulting counter-traction force is transmitted down collapsible rigid tube (104) to framesheet (10) long-axis tube pocket (16) end which then balances applied counter-traction forces throughout enveloping framesheet (10) as closure occurs with plurality of dynamic closure strap (106). Traction is only integrated in present invention to overcome unopposed muscle contraction, not to immobilize the injured extremity. Immobilization is accomplished by the enveloping framesheet (10) made rigid by the collapsible rigid tube (104) secured to the extremity by the dynamic closure straps (106).

When traction is manually applied to traction bar (110), cantilever arm (30) compresses pre-calibrated 316 stainless steel compression spring (34) on indicator spring post (52) against spring stop (118) and the amount of compression is indicated by the movement of the dowel pin (36) within the pin indicator slot (40). The dowel pin is marked to indicate specific quantified amounts of pressure in pounds using a calibration mark (32), and a visual ring indicator (114). The indicator marks show are adapted to mark when seven and fifteen pounds of pressure are applied as traction to the extremity. Traction greater than fifteen pounds can be applied, but not reflected in the indicators. Such traction pressures are not recommended within standard of orthopedic care.

Off-axis adaptor (120) provides an articulating joint in the collapsible rigid tube (104) for stabilizing upper and lower extremity joint injury in a bent position. Off-axis adaptor (120) is inserted by pulling collapsible rigid tube (104) internal ferrule assembly (100) away from tube (20) and inserting elastic cord (24) into elastic cord slot (122) then sliding off-axis adaptor (120) onto internal ferrule assembly (100) and allowing tube (20) to return against off-axis adaptor (120) rounded articulating tip (126) as shown in FIG. 6A. Collapsible rigid tube (104) is then inserted into posterior long-axis tube pocket (16), placed on injured extremity in position found with dynamic closure strap (106) applied in plurality from proximal to distal, crossing straps where necessary to maintain immobilization angle with enough force to actuate elastic belting (66) to provide a custom fitting posterior enveloping off-axis support platform. Injured upper extremity is secured to torso by anatomic stabilizer (128) with dynamic closure strap (106) for additional support and to maintain casualty mobility. Injured lower extremity is secured to uninjured lower extremity by anatomic stabilizer (128) with dynamic closure strap (106) to maintain off-axis position of comfort during evacuation.

Emergency quick splint framesheet (10) integrates anatomic stabilizer (128) with dynamic closure strap (106) to provide for proximal upper and lower long bone extremity joint immobilization. Anatomic stabilizer (128) with dynamic closure strap (106) circumferentially binds proximal upper extremity to torso effectively immobilizing shoulder joint above. Lower extremity proximal hip joint is immobilized by sliding anatomic stabilizer (128) under lower back lumbar region, working inferior under pelvis into position over trochanters, and applying circumferential compression with dynamic closure strap (106) to securely immobilize hip joint above framesheet (10), while said framesheet (10) immobilizes fracture site and distal joints within said emergency quick splint framesheet (10).

Figure 8:
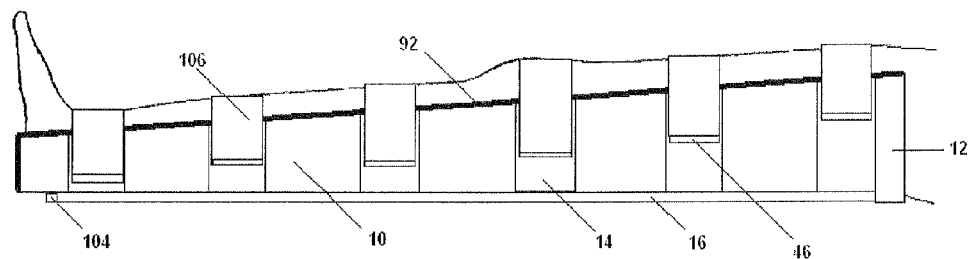
FIG. 8 shows the device of the present invention assembled on a limb (134) of a patient.
Figure 9:
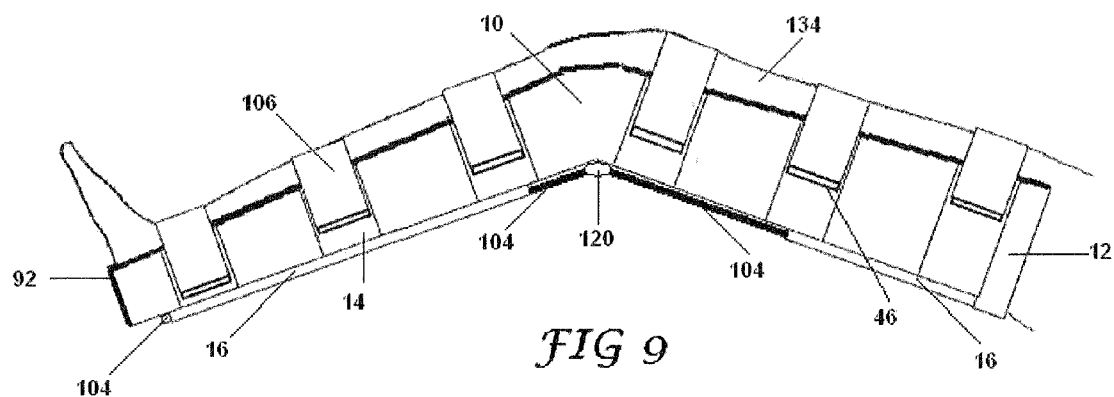
FIG. 9 shows the device of the present invention assembled on a limb in off-axis formable immobilization.
Figure 10:
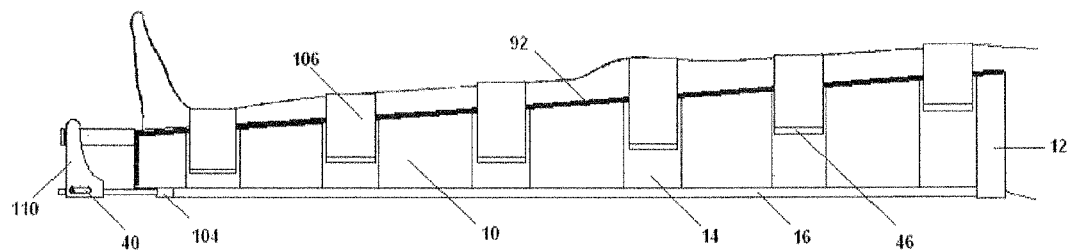
FIG. 10 shows the device of the invention to apply traction to the limb of a patient.

FIG. 8. Shows the device of the present invention assembled on the limb of a patient.

CONCLUSION, RAMIFICATIONS, AND SCOPE

It is understood that variations from form of present invention preferred embodiment disclosed herein may be made without departure from spirit and scope of present invention, and that detailed specification and drawings are to be considered as merely illustrative rather than limiting. Thus by way of example and not limitation, framesheet (10) may be constructed from hydrophobic mesh materials to provide for visualization of injured extremity, provide continuous extremity cooling in hot environments, or WMD chemical and biological decontamination without splint removal. Plurality of dynamic closure straps (106) could be attached to prevent loss, or constructed as part of framesheet (10) using different sizes to permit reshaping of framesheet (10). Collapsible rigid tube (104) could have fixed length detachable traction bar with cantilever end. Traction bar (110) rod (28) could be machined with long-axis ratchet type groove to receive external trigger release slide-lock that when applied press fits on end of tube (20) allowing traction bar (110) to slide in and out of collapsible rigid tube (104) with quick ratchet type length adjustment. Collapsible rigid tube (104) could be constructed in a manner that completely disassembles or telescopes rather than folding using internal twist-lock assembly (96) or external compression locking mechanism to maintain compactness.

Various features and advantages of present invention are thought to be clear from foregoing description. Various other features and advantages not specifically enumerated will undoubtedly occur to those versed in the art, as likewise will variations and modifications of preferred embodiment illustrated and described, all of which may be achieved without departing from spirit and scope of invention as defined by following claims. General design of individual parts of invention as explained above may be varied in accordance with requirements in regard to manufacture and production, while still remaining within spirit and principle of invention, without prejudicing novelty thereof.

I claim:

1. A rapid deployment splint for an injured extremity, wherein the extremity has an anatomy, the splint comprising:
    a framesheet consisting essentially of a fabric material and having a shape generally corresponding to the anatomy of the extremity, wherein the framesheet has a textured first surface adapted to contact the injured extremity;
    at least one closure strap having an elastic portion coupled to the framesheet and configured to adjustably secure the framesheet about the injured extremity with enough force to actuate the elastic portion of the closure strap, wherein the tension from the actuated elastic portion wraps the framesheet around a length of the extremity such that the contour of the framesheet envelopes a length of the extremity with a custom fit;
    a rigid insert;
    a pocket coupled to the framesheet on a second surface opposite the first surface, wherein the rigid insert fits into the pocket;
    a cantilever coupled to the rigid insert; and
    a harness, detachably coupled to the cantilever, wherein the harness is adapted to surround the extremity and apply a traction force to the extremity.

2. The rapid deployment splint of claim 1, wherein the fabric material is substantially composed of a buff textured hydrophobic fabric.

3. The rapid deployment splint of claim 1, wherein the cantilever includes an indicator to display a quantity of applied traction force.

4. The rapid deployment splint of claim 1, wherein the splint further comprises a padded base band coupled to or housed within the framesheet.

5. The rapid deployment splint of claim 1, wherein the closure strap includes an elastic portion.

6. The rapid deployment splint of claim 1, wherein the cantilever is detachably coupled to the rigid insert.

7. The rapid deployment splint of claim 1 wherein the rigid insert is collapsible into at least two segments.

8. The rapid deployment splint of claim 1, further comprising an off-axis adaptor coupled to the rigid insert to allow the rigid insert to have a fixed angle.

9. The rapid deployment splint of claim 7, further comprising an off-axis adaptor to allow the rigid insert to have a fixed angle, wherein the rigid insert is adapted to detachably couple to the off-axis adaptor.

10. The rapid deployment splint of claim 1, further comprising a stabilizer.

11. The rapid deployment splint of claim 10, wherein the stabilizer is separate from and unattached to the rest of the rapid deployment splint.

12. A rapid deployment splint to optionally treat a first extremity and a second extremity, wherein the first extremity has a greater length than the second extremity, the splint comprising:
    a framesheet consisting essentially of a fabric material and having a shape generally corresponding to the anatomy of the first extremity, wherein the framesheet has a textured first surface adapted to contact the first extremity and at least one fold line such that folding the framesheet at the at least one fold line adjusts the framesheet to present a second textured surface adapted to contact the second extremity, the second surface generally corresponding to the anatomy of the second extremity;
    at least one adjustable closure strap having an elastic portion coupled to the framesheet and configured to secure the framesheet about either the first extremity or the second extremity with enough force to actuate the elastic portion of the closure strap, wherein tension from the actuated elastic portion wraps the framesheet around a length of either the first extremity or the second extremity such that the contour of the framesheet envelopes a length of the extremity with a custom fit;
    a rigid insert, wherein the rigid insert is collapsible into at least two segments;
    a pocket coupled to the framesheet, wherein the rigid insert fits into the pocket;
    a cantilever coupled to the rigid insert; and
    a harness, detachably coupled to the cantilever, wherein the harness is adapted to optionally surround either the first injured extremity or the second injured extremity and apply a traction force to the injured extremity and wherein the first surface and second surface are textured to distribute a counter traction force through a first portion of the first surface in contact with the first extremity or a second portion of the second surface in contact with the second extremity.

13. The rapid deployment splint of claim 12, wherein the splint further comprises an off axis adapter to allow the rigid insert to have a fixed angle.

14. The rapid deployment splint of claim 12, further comprising a stabilizer.

15. The rapid deployment splint of claim 14, wherein the stabilizer is separate from and unattached to the rest of the rapid deployment splint.

16. The rapid deployment splint of claim 12, further comprising a padded base band.

17. A method of immobilizing an injured extremity having a joint, a proximal end and a distal end, the method comprising:
    providing a framesheet consisting essentially of a fabric material having a shape generally corresponding to the anatomy of the extremity, wherein the framesheet has a textured first surface adapted to contact the extremity, and a second surface coupled to a pocket;
    providing at least one closure strap having an elastic portion coupled to the framesheet;
    inserting a rigid insert into the pocket;

placing the framesheet posterior to the extremity, such that the first surface contacts the extremity;

securing a portion of the framesheet about the extremity with enough force to actuate the elastic portion of the closure strap such that tension from the actuated elastic portion wraps the framesheet substantially around the extremity at a position adjacent to the proximal end of the extremity;

attaching a cantilever to an end of rigid insert adjacent to the distal end of the extremity;

applying traction to the extremity using the cantilever and a harness detachably coupled to the cantilever;

gripping the extremity with the textured first surface to distribute counter traction forces; and further securing the framesheet about the extremity such that the framesheet substantially surrounds the extremity.

18. The method of claim 17, further comprising providing a traction indicator and monitoring the amount of traction applied to the extremity using the indicator.

19. The method of claim 18, further comprising providing a mark on the traction indicator corresponding to a desired amount of traction.

20. The method of claim 17, further comprising providing a stabilizer to at least partially immobilize a joint of the extremity.

* * * * *